US011202567B2

(12) United States Patent
Glik et al.

(10) Patent No.: US 11,202,567 B2
(45) Date of Patent: Dec. 21, 2021

(54) RETINAL CAMERA WITH LIGHT BAFFLE AND DYNAMIC ILLUMINATOR FOR EXPANDING EYEBOX

(71) Applicant: Verily Life Sciences LLC, South San Francisco, CA (US)

(72) Inventors: Eliezer Glik, San Francisco, CA (US); Sam Kavusi, Menlo Park, CA (US)

(73) Assignee: Verily Life Sciences LLC, South San Francisco, CA (US)

(*) Notice: Subject to any disclaimer, the term of this patent is extended or adjusted under 35 U.S.C. 154(b) by 222 days.

(21) Appl. No.: 16/457,191

(22) Filed: Jun. 28, 2019

(65) Prior Publication Data

US 2020/0015676 A1 Jan. 16, 2020

Related U.S. Application Data

(60) Provisional application No. 62/698,457, filed on Jul. 16, 2018.

(51) Int. Cl.
*A61B 3/15* (2006.01)
*A61B 3/00* (2006.01)

(52) U.S. Cl.
CPC ............ *A61B 3/152* (2013.01); *A61B 3/0008* (2013.01); *A61B 3/0091* (2013.01); *A61B 3/156* (2013.01); *A61B 3/0058* (2013.01); *A61B 3/0083* (2013.01)

(58) Field of Classification Search
CPC ..... A61B 3/152; A61B 3/0008; A61B 3/0091; A61B 3/156; A61B 3/0083; A61B 3/0058; A61B 3/14; A61B 3/12
(Continued)

(56) References Cited

U.S. PATENT DOCUMENTS

| 5,585,873 A | 12/1996 | Shalon et al. |
| 7,677,730 B2 | 3/2010 | Shimizu |

(Continued)

FOREIGN PATENT DOCUMENTS

| WO | 2012018991 A2 | 2/2012 | |
| WO | WO-2012018991 A2 * | 2/2012 | ............... A61B 3/14 |

(Continued)

OTHER PUBLICATIONS

DeHoog, E., and J. Schwiegerling, "Optimal Parameters for Retinal Illumination and Imaging in Fundus Cameras," Applied Optics 47(36):6769-6777, Dec. 2008.

(Continued)

*Primary Examiner* — Mohammed A Hasan
(74) *Attorney, Agent, or Firm* — Christensen O'Connor Johnson Kindness PLLC

(57) ABSTRACT

A retinal imaging system includes an image sensor for acquiring a retinal image and a dynamic illuminator for illuminating a retina to acquire the retinal image. The dynamic illuminator includes a center baffle along with first and second illumination arrays. The center baffle extends from and surrounds an aperture through which an image path for the retinal image passes before reaching the image sensor. The first illumination array extends out from first opposing sides of the aperture along a first linear axis. The second illumination array extends out from second opposing sides of the aperture along a second linear axis that is substantially orthogonal to the first linear axis.

28 Claims, 13 Drawing Sheets

(58) Field of Classification Search
USPC .......................................................... 351/208
See application file for complete search history.

(56) References Cited

U.S. PATENT DOCUMENTS

| | | |
|---|---|---|
| 8,708,490 B2 | 4/2014 | Baranton et al. |
| 9,743,832 B2 | 8/2017 | de Paz Sicam et al. |
| 2013/0057828 A1* | 3/2013 | de Smet ................... A61B 3/12 |
| | | 351/207 |
| 2016/0029887 A1* | 2/2016 | Su ........................ A61B 3/0008 |
| | | 351/206 |
| 2017/0164830 A1 | 6/2017 | Huang et al. |

FOREIGN PATENT DOCUMENTS

| | | | | |
|---|---|---|---|---|
| WO | 2014127134 A1 | 8/2014 | | |
| WO | WO-2014127134 A1 * | 8/2014 | ............... | A61B 3/12 |
| WO | 2017025583 A1 | 2/2017 | | |
| WO | WO-2017025583 A1 * | 2/2017 | ............... | A61B 3/12 |

OTHER PUBLICATIONS

International Search Report and Written Opinion, dated Oct. 17, 2019, for corresponding International Patent Application No. PCT/US2019/040606, 7 pages.

* cited by examiner

RETINAL CAMERA WITH LIGHT BAFFLE AND DYNAMIC ILLUMINATOR FOR EXPANDING EYEBOX

CROSS-REFERENCE TO RELATED APPLICATIONS

This application claims the benefit of U.S. Application No. 62/698,457, filed on Jul. 16, 2018, the contents of which are incorporated herein by reference.

TECHNICAL FIELD

This disclosure relates generally to retinal imaging technologies, and in particular but not exclusively, relates to illumination techniques for retinal imaging.

BACKGROUND INFORMATION

Retinal imaging is a part of basic eye exams for screening, field diagnosis, and progress monitoring of many retinal diseases. A high fidelity retinal image is important for accurate screening, diagnosis, and monitoring. Bright illumination of the posterior interior surface of the eye (i.e., retina) through the pupil improves image fidelity but often creates optical aberrations or image artifacts, such as corneal reflections, iris reflections, or lens flare, if the retinal camera and illumination source are not adequately aligned with the eye. Simply increasing the brightness of the illumination does not overcome these problems, but rather makes the optical artifacts more pronounced, which undermines the goal of improving image fidelity.

Accordingly, camera alignment is very important, particularly with conventional retinal cameras, which typically have a very limited eyebox due to the need to block the deleterious image artifacts listed above. The eyebox for a retinal camera is a three dimensional region in space typically defined relative to an eyepiece of the retinal camera and within which the center of a pupil or cornea of the eye should reside to acquire an acceptable image of the retina. The small size of conventional eyeboxes makes retinal camera alignment difficult and patient interactions during the alignment process often strained.

Various solutions have been proposed to alleviate the alignment problem. For example, moving/motorized stages that automatically adjust the retina-camera alignment have been proposed. However, these stages tend to be mechanically complex and substantially drive up the cost of a retinal imaging platform. An effective and low cost solution for efficiently and easily achieving eyebox alignment of a retinal camera would improve the operation of retinal cameras.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Embodiments of a system, apparatus, and method of operation of a retinal camera with a dynamic illuminator having an expanded eyebox are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Figure 1:
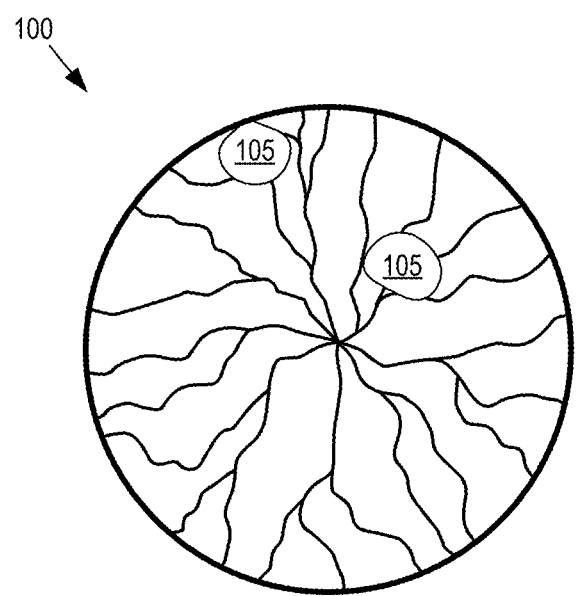
FIG. 1 illustrates a retinal image including an image artifact, in accordance with an embodiment of the disclosure.

High fidelity retinal images are important for screening, diagnosing, and monitoring many retinal diseases. To this end, reducing or eliminating instances of image artifacts that occlude, or otherwise malign portions of the retinal image is desirable. FIG. 1 illustrates an example retinal image 100 with multiple image artifacts 105. These image artifacts may arise when misalignment between the retinal imaging system and the eye permit stray light and deleterious reflections from the illumination source to enter the image path and ultimately are captured by the image sensor with the retinal image light. Misalignment can lead to deleterious corneal/iris reflections, refractive scattering from the crystalline lens, and occlusion of the imaging aperture.

Conventional imaging systems have relatively small eyeboxes, which require precise alignment to avoid image artifacts from entering the image path. Embodiments described herein provide a dynamic illuminator that changes its illumination pattern based upon a detected alignment between the retinal imaging system and an eye. These dynamic changes in the illumination pattern expand the eyebox without use of complicated or costly mechanical components. The expanded eyebox eases the alignment burden while reducing the instances of image artifacts occluding or otherwise maligning the captured retinal image. The dynamic illuminator combines two different illumination architectures—one when the eye is roughly aligned with the optical axis or gaze direction of the eye (referred to herein as a circular illumination pattern) and one when the eye is offset from the optical axis or gaze direction of the eye (referred to herein as a non-circular illumination pattern or stacked illumination). By dynamically switching between these two illumination architectures, the eyebox of the retinal imaging system described herein may be expanded by 2× or more over conventional ring illuminators.

Figure 2:
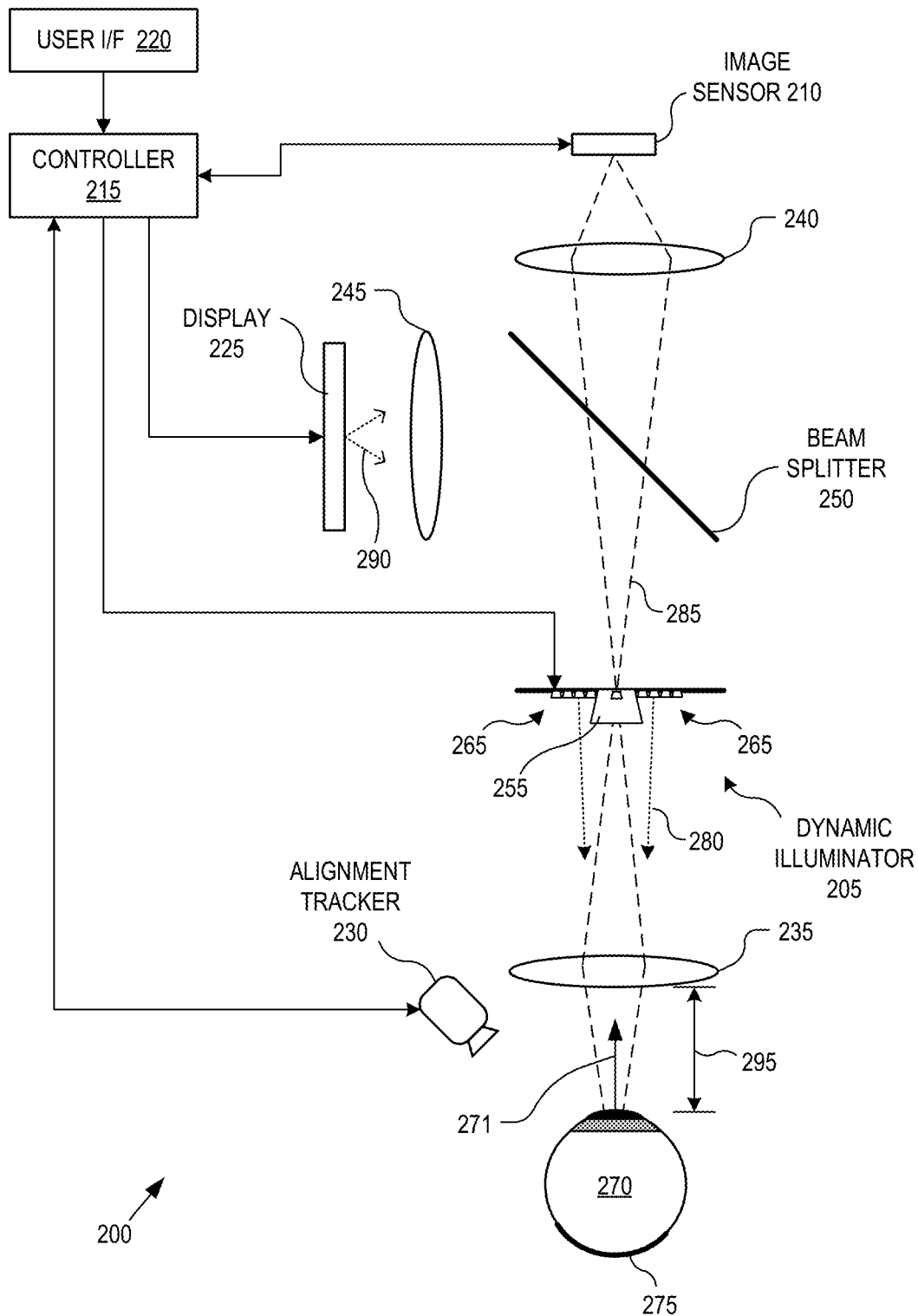
FIG. 2 illustrates a retinal imaging system with a dynamic illuminator, in accordance with an embodiment of the disclosure.

FIG. 2 illustrates a retinal imaging system 200 with a dynamic illuminator, in accordance with an embodiment of the disclosure. The illustrated embodiment of retinal imaging system 200 includes a dynamic illuminator 205, an image sensor 210 (also referred to as a retinal camera sensor), a controller 215, a user interface 220, a display 225, an alignment tracker 230, and an optical relay system. The illustrated embodiment of the optical relay system including lenses 235, 240, 245 and a beam splitter 250. The illustrated embodiment of dynamic illuminator 205 includes a center baffle 255 surrounding an aperture and illumination arrays 265 extending from center baffle 255.

The optical relay system serves to direct (e.g., pass or reflect) illumination light 280 output from dynamic illuminator 205 along an illumination path through the pupil of eye 270 to illuminate retina 275 while also directing image light 285 of retina 275 (i.e., the retinal image) along an image path to image sensor 210. Image light 285 is formed by the scattered reflection of illumination light 280 off of retina 275. In the illustrated embodiment, the optical relay system further includes beam splitter 250, which passes at least a portion of image light 285 to image sensor 210 while also directing display light 290 output from display 225 to eye 270. Beam splitter 250 may be implemented as a polarized beam splitter, a non-polarized beam splitter (e.g., 90% transmissive and 10% reflective, 50/50 beam splitter, etc.), a dichroic beam splitter, or otherwise. The optical relay system includes a number of lenses, such as lenses 235, 240, and 245, to focus the various light paths as needed. For example, lens 235 may include one or more lensing elements that collectively form an eyepiece that is displaced from the cornea of eye 270 by an eye relief 295 during operation. Lens 240 may include one or more lens elements for bring image light 285 to a focus on image sensor 210. Lens 245 may include one or more lens elements for focusing display light 290. It should be appreciated that optical relay system may be implemented with a number and variety of optical elements (e.g., lenses, reflective surfaces, diffractive surfaces, etc.).

In one embodiment, display light 290 output from display 225 is a fixation target or other visual stimuli. The fixation target not only can aid with obtaining alignment between retinal imaging system 200 and eye 270 by providing visual feedback to the patient, but may also give the patient a fixation target upon which the patient can accommodate their vision. Display 225 may be implemented with a variety of technologies including an liquid crystal display (LCD), light emitting diodes (LEDs), various illuminated shapes (e.g., an illuminated cross or concentric circles), or otherwise.

Controller 215 is coupled to image sensor 210, display 225, dynamic illuminator 205, and alignment tracker 230 to choreograph their operation. Controller 215 may include software/firmware logic executing on a microcontroller, hardware logic (e.g., application specific integrated circuit, field programmable gate array, etc.), or a combination of software and hardware logic. Although FIG. 2 illustrates controller 215 as a distinct functional element, the logical functions performed by controller 215 may be decentralized across a number hardware elements. Controller 115 may further include input/output (I/O ports), communication systems, or otherwise. Controller 215 is coupled to user interface 220 to receive user input and provide user control over retinal imaging system 200. User interface 220 may include one or more buttons, dials, feedback displays, indicator lights, etc.

Image sensor 210 may be implemented using a variety of imaging technologies, such as complementary metal-oxide-semiconductor (CMOS) image sensors, charged-coupled device (CCD) image sensors, or otherwise. In one embodiment, image sensor 210 includes an onboard memory buffer or attached memory to store retinal images.

Alignment tracker 230 operates to track alignment between retinal imaging system 200 and eye 270. Alignment tracker 230 may operate using a variety of different techniques to track the relative positions of eye 270 and retinal imaging system 200 including pupil tracking, retina tracking, iris tracking, or otherwise. In one embodiment, alignment tracker 230 includes one or more infrared (IR) emitters to track eye 270 via IR light while retinal images are acquired with visible spectrum light. In such an embodiment, IR filters may be positioned within the image path to filter the IR tracking light. In other embodiments, the tracking illumination is temporally offset from image acquisition.

During operation, controller 115 operates dynamic illuminator 105 and retinal camera 110 to capture one or more retinal images. Dynamic illuminator 105 is dynamic in that its illumination pattern is not static; but rather, is dynamically changed under the influence of controller 215 based upon the determined alignment with eye 270 (discussed in detail below). Illumination light 280 is directed through the pupil of eye 270 to illuminate retina 275. The scattered reflections from retina 275 are directed back along the image path through an aperture in center baffle 255 to image sensor 210. Center baffle 255 operates to block deleterious reflections and light scattering that would otherwise malign the retinal image while passing the image light itself. The illumination patterns output by dynamic illuminator 205 are selected based upon the current alignment to reduce deleterious image artifacts. Image artifacts may arise from light scattering by the human lens within eye 270, reflections from the cornea/iris, or even direct specular reflections of illumination light 280 from retina 275. Direct specular reflections from retina 275 or the cornea/iris can create washed out regions (e.g., image artifacts 105) in the retinal image. The dynamic changes in the illumination patterns output from dynamic illuminator 205 serve to direct these specular reflections off axis from the image path and therefore blocked by the field stop or center baffle 255.

Figure 3:
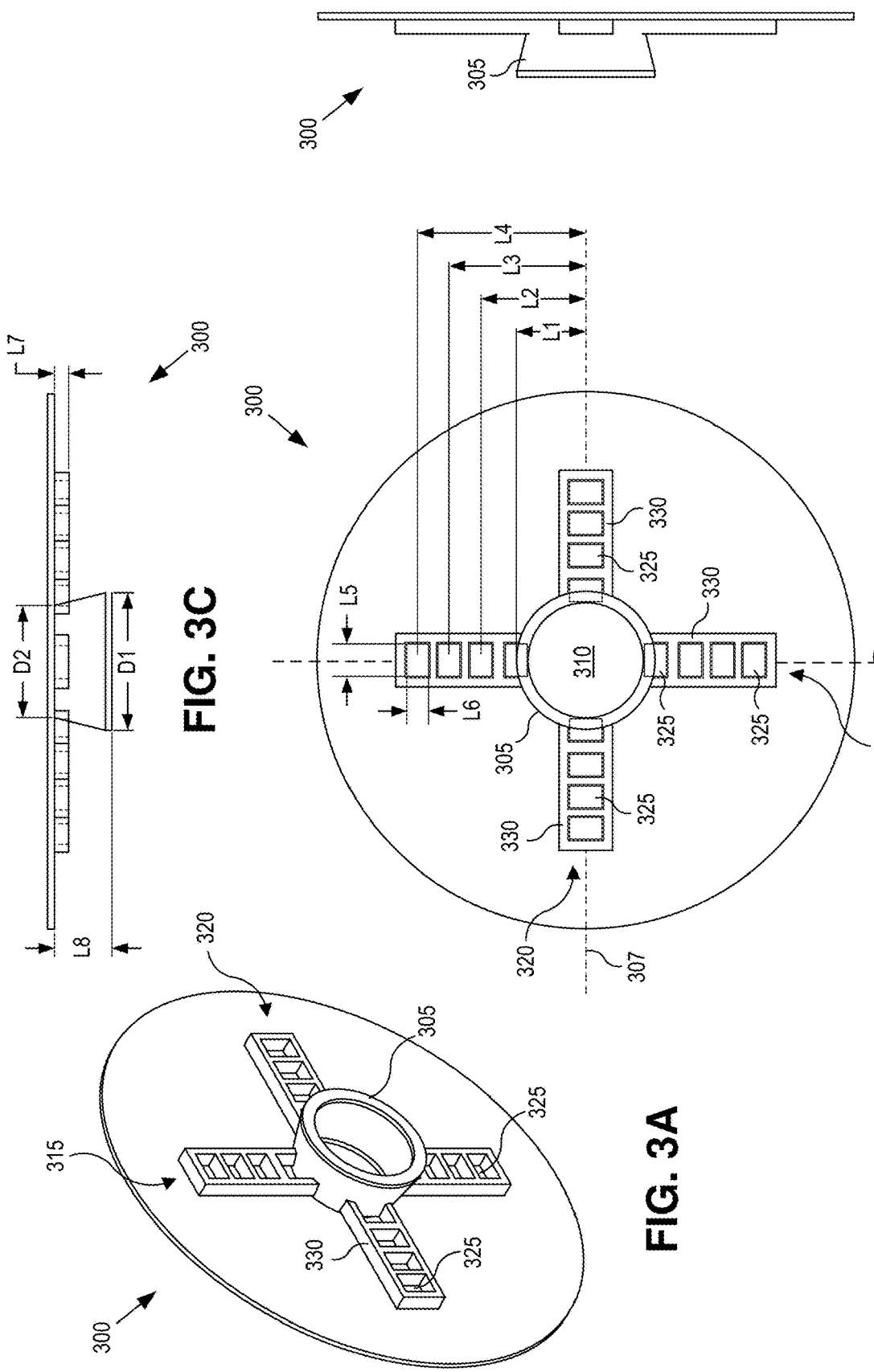
FIGS. 3A-D illustrate various views of a dynamic illuminator having a center baffle surrounded by illumination arrays, in accordance with an embodiment of the disclosure.

FIGS. 3A-D illustrate various views of a dynamic illuminator 300, in accordance with an embodiment of the disclosure. The illustrated embodiment of dynamic illuminator 300 is one possible implementation of dynamic illuminator 205 in FIG. 2. FIG. 3A is a perspective view illustration of dynamic illuminator 300, FIG. 3B is a plan view illustration, FIG. 3C is a cross-sectional illustration, and FIG. 3D is a side view illustration of the same. The illustrated embodiment of dynamic illuminator 300 includes a center baffle 305 defining an aperture 310, a first illumination array 315 extending out (e.g., radially) from opposing sides of aperture 310 and center baffle 305 along a first linear axis 306 (vertical axis in FIG. 3B), and a second illumination array 320 extending out (e.g., radially) from opposing sides of aperture 310 and center baffle 305 along a second linear axis 307 (horizontal axis in FIG. 3B). Each illumination array 315 and 320 includes discrete illumination sources 325 that are each encircled by illumination baffles 330.

As mentioned, dynamic illuminator 300 includes arrays of illumination sources 325 that extend out from center baffle 305 to provide the source of light for illuminating retina 275. In the illustrated embodiment, illumination arrays 315 and 320 extend along substantially orthogonal linear axes 306 and 307, respectively, forming a sort of plus sign or cross-like shape. In the illustrated embodiment, linear axes 306 and 307 are radial lines that pass substantially through the center of aperture 310. In one embodiment, illumination sources 325 within illumination array 315 are symmetrically positioned about linear axis 307 while illumination sources 325 within illumination array 320 are symmetrically positioned about linear axis 306. Each illumination array includes two sections that extend from opposing sides of center baffle 305 and aperture 310. Illumination arrays 315 and 320 include discrete locations of independently controlled illumination. In other words, illumination sources 325 can be independently enabled or disabled under the influence of controller 215 to generate distinct illumination patterns. In one embodiment, illumination sources 325 are implemented as distinct LED sources. In other embodiments, illumination sources 325 may be implemented with a variety of technologies and configurations capable of providing distinct locations of independently controllable illumination light. For example, each section of the illumination arrays 315 and 320 may share a common backlight, but have controllable masks (e.g., LCD screens) to selectively filter and control the location of light illumination. Other illumination technologies may be used. Furthermore, although each illumination array 315 and 320 is illustrated as including eight illumination sources 325, implementations may include more or less illumination sources 325. In one embodiment, illumination sources 325 have the following separation pitches and sizes: L1=6.5 mm, L2=10 mm, L3=13 mm, L4=16 mm, L5=3 mm, and L6=2 mm. Of course, other sizes and separation pitches may be implemented.

In the illustrated embodiment, center baffle 305 has a cone shape that surrounds and extends out towards the eyepiece lens 235 from aperture 310. The sides of center baffle 305 overlap a portion of the inner most illumination sources 325 that are immediately adjacent to center baffle 305. This partial overlap causes center baffle 305 to partially block or cast a shadow when backlit by the innermost illumination sources 325, but does not block the other illumination sources 325. The shadow serves to substantially separate and isolate the image path from the illumination path thus reducing the crosstalk between these paths and reducing image artifacts in the retinal images. When the innermost illumination sources 325 are illuminated, center baffle 305 blocks illumination ray angles that create poor image quality due to scattering in the eye lens and reflections from the cornea.

Deleterious image artifacts are further isolated and reduced by the use of illumination baffles 330 surrounding each illumination source 325. Illumination baffles 330 serve to constrain the emission divergence pattern of illumination sources 325, and in some embodiments also constrain the effective die size of illumination sources 325 by covering over portions of each illumination source 325. Illumination baffles 330 also reduce the dependence of the illumination path on fabrication deviances/tolerances between batches or instances of the discrete illumination sources 325 particularly since many LED sources, or other types of illumination sources, do not generate a precise illumination pattern or collimated light. Illumination baffles 330 may be implemented as discrete baffles or part of an integrated shroud or molding assembly. The molding assembly may include a discrete molding for each half of a given illumination array 315 or 320, or alternatively, illumination baffles 330 along with center baffle 305 may be fabricated from a single contiguous assembly. In the illustrated embodiment, center baffle 305 has a circular cross-sectional shape (about a center optical axis of the image path passing through aperture 310) while illumination baffles 330 have a rectangular cross-sectional shape. Of course, other cross-sectional shapes may be used to fine tune the illumination and image paths. For example, illumination baffles 330 may also have a circular cross-sectional shape. In one embodiment, center baffle 305 and illumination baffles 330 have the following dimensions: D1=13 mm, D2=10.60 mm, L5=3 mm, L6=2 mm, L7=1.5 mm, L8=5.5 mm. Of course, other dimensions may be implemented.

Figure 4:
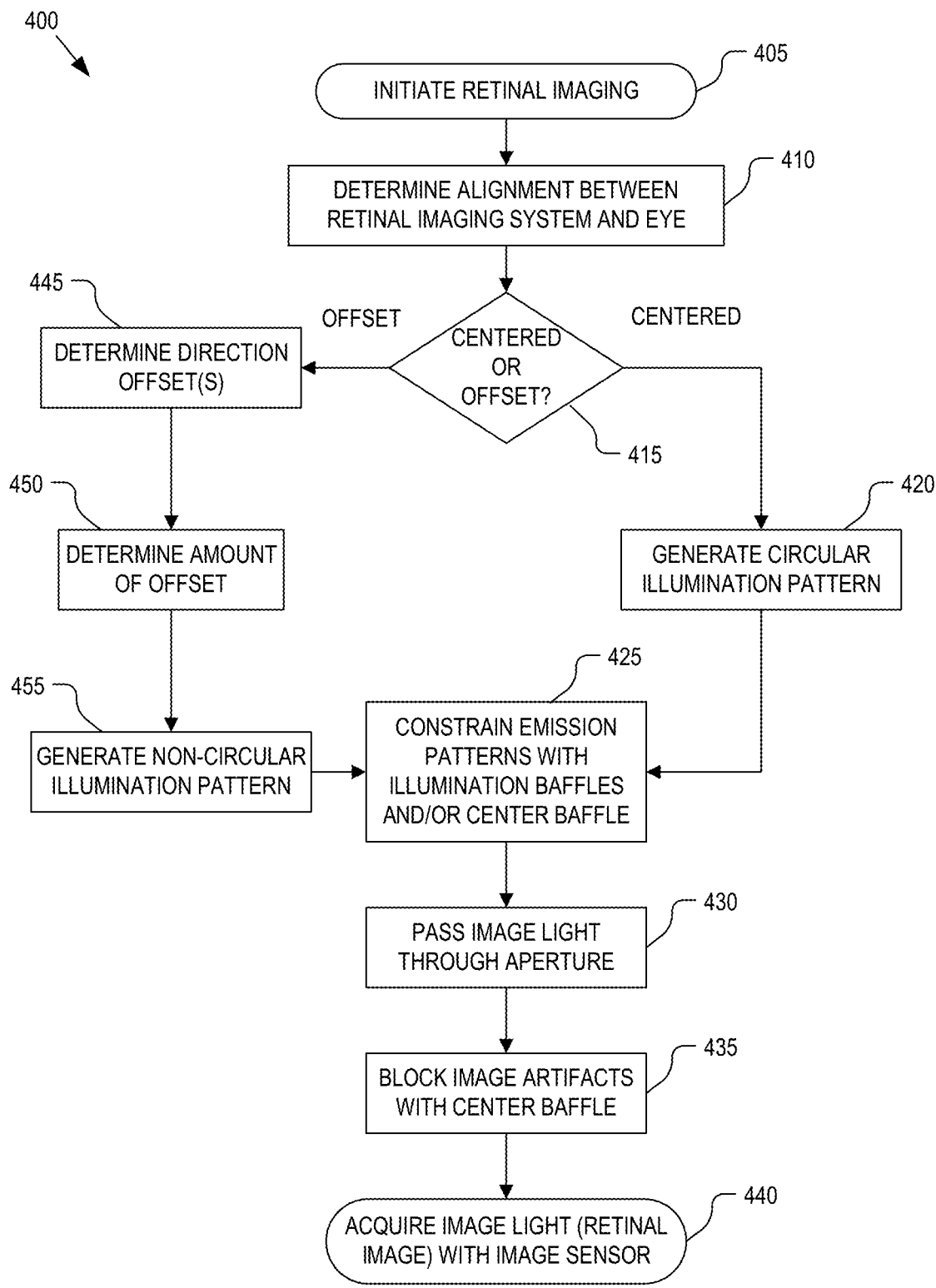
FIG. 4 is a flow chart illustrating operation of the retinal imaging system, in accordance with an embodiment of the disclosure.

FIG. 4 is a flow chart illustrating a process 400 for operation of retinal imaging system 200, in accordance with an embodiment of the disclosure. The order in which some or all of the process blocks appear in process 400 should not be deemed limiting. Rather, one of ordinary skill in the art having the benefit of the present disclosure will understand that some of the process blocks may be executed in a variety of orders not illustrated, or even in parallel.

In a process block 405, the retinal imaging process is initiated. Initiation may include the user selecting a power button from user interface 220. In a process block 410, alignment tracker 230 commences tracking and determining the alignment between retinal camera system 200 and eye 270. In particular, tracking may be determined as a relative measurement between eyepiece lens 235 and the pupil, iris, or retina of eye 270. A variety of different alignment tracking techniques may be implemented including pupil tracking, iris tracking, retinal tracking, trial and error, etc. The alignment tracking is used to determine, which of at least two illumination schemes should be used for illuminating retina 275 during image acquisition. The transition between these illumination schemes may be abrupt or a smooth fading there between as the relative alignment wanders between a central alignment and an offset alignment.

Figure 5C:
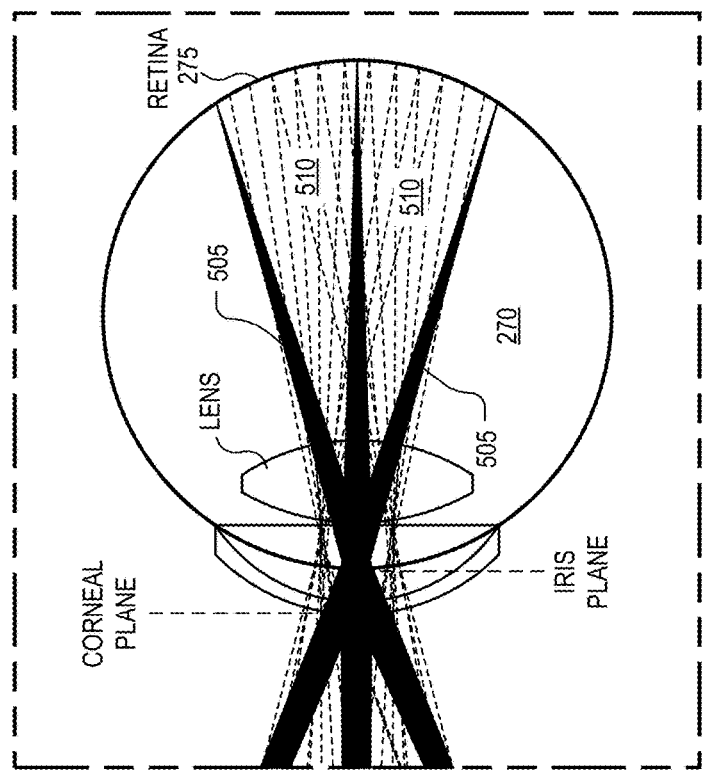
FIG. 5C illustrates reduced overlap between the image path and the illumination paths at the cornea, iris, and lens with a circular illumination pattern, in accordance with an embodiment of the disclosure.
Figure 5A:
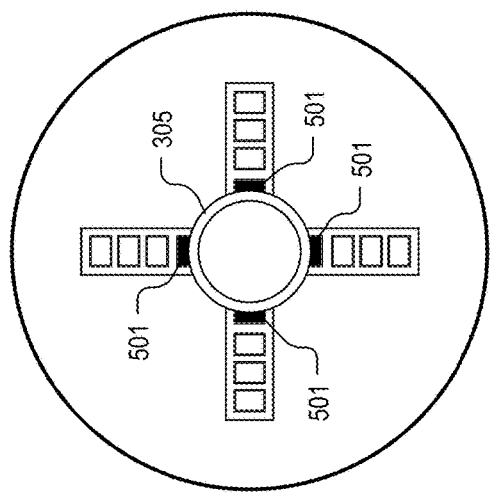
FIGS. 5A & 5B illustrate a circular illumination pattern from the dynamic illuminator when the retinal imaging system is centrally aligned with a gaze direction of an eye, in accordance with an embodiment of the disclosure.
Figure 5B:
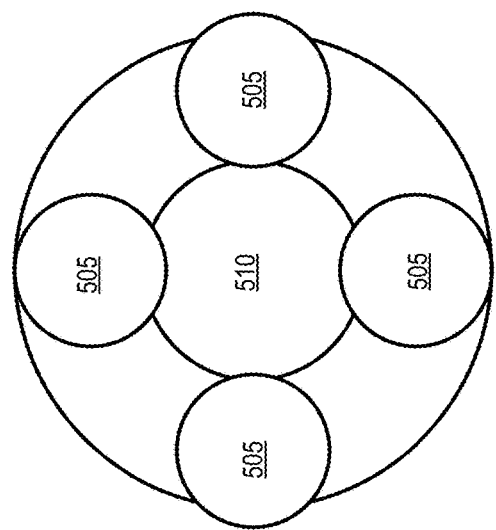

In decision block 415, if retinal camera system 200 is determined to be centrally aligned with the gaze direction 271 (e.g., optical axis of eye 270) within a defined threshold, then process 400 continues to a process block 420. In process block 420, dynamic illuminator 205 is operated by controller 215 to generate a circular illumination pattern for illuminating retina 275 through the pupil of eye 270. FIGS. 5A-C illustrate characteristics of the circular illumination pattern. As illustrated in FIG. 5A, the circular illumination pattern simultaneously illuminates the inner most illumination sources 501 immediately adjacent to center baffle 305 (or 255) while disabling or not illuminating the remaining outer illumination sources 325 not immediately adjacent to center baffle 305. As illustrated in FIG. 5B, the illumination paths 505 are substantially separated or isolated from the image path 510 at the iris, lens, and cornea.

The emission divergence patterns of illumination sources 501 are constrained and controlled by illumination baffles 330 and a shadow cast by center baffle 305 (process block 425). Center baffle 305 serves to block the portion of the illumination light output from inner illuminator sources 501 that would cause deleterious scattering in eye 270. As further illustrated in FIG. 5C, illumination paths 505 are substantially separated from image path 510 (e.g., physically offset from each other) at the regions in eye 270 that are susceptible to creation of image artifacts. These regions include the corneal plane, the iris plane, and the lens. Center baffle 305 strategically casts an illumination shadow onto these eye structures that reduces crosstalk between the image path 510 and illumination paths 505 to reduce image artifacts captured by image sensor 210. The angle and depth of center baffle 305 influences the separation of the image path and the illumination path at the cornea, iris and crystalline lens. The angle and depth may be selected to achieve a particular separation range.

In process block 430, the retinal image passes through aperture 310 where center baffle 305 further blocks deleterious reflections and other stray refractions (process block 435) before image sensor 210 captures image light 285 forming the retinal image.

Figure 6C:
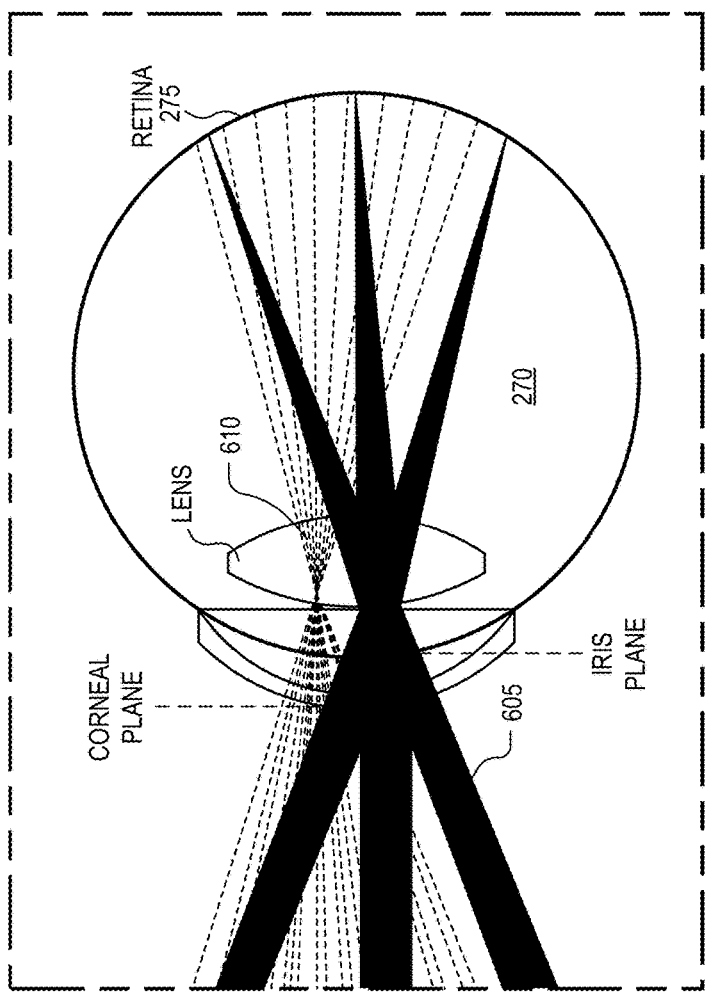
FIG. 6C illustrates reduced overlap between the image path and the illumination path at the cornea, iris, and lens with a non-circular illumination pattern, in accordance with an embodiment of the disclosure.
Figure 6A:
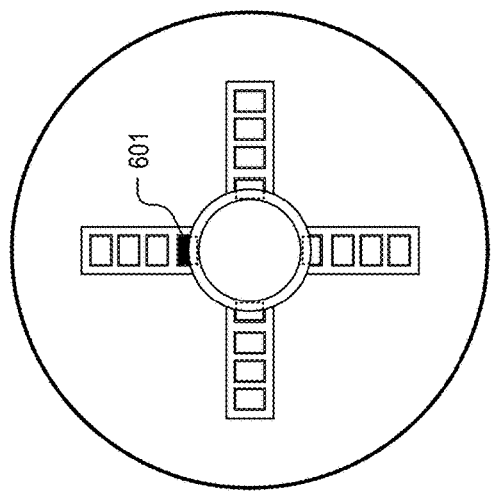
FIGS. 6A & 6B illustrate a non-circular illumination pattern from the dynamic illuminator when the retinal imaging system is offset from a gaze direction in a single direction, in accordance with an embodiment of the disclosure.
Figure 6B:
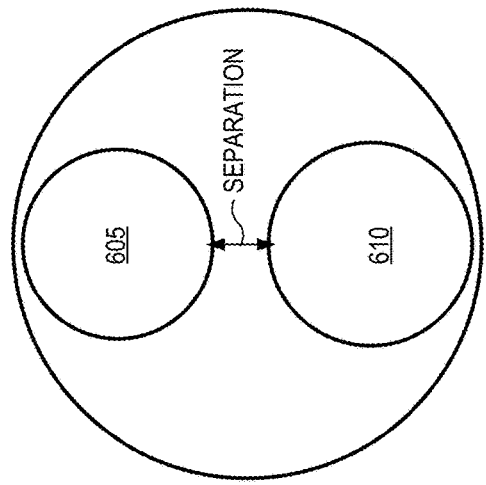
Figure 7A:
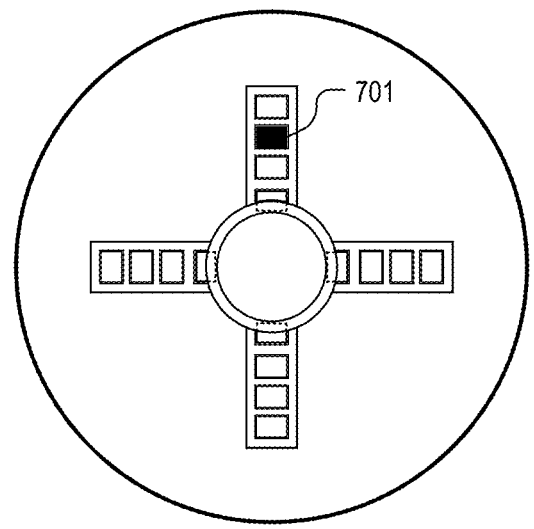
FIG. 7A illustrates a non-circular illumination pattern from the dynamic illuminator when the retinal imaging system is offset from a gaze direction in a single direction by a larger magnitude, in accordance with an embodiment of the disclosure.

Returning to decision block 415, if retinal camera system 200 is determined to be offset from the gaze direction 271 by a defined threshold, then process 400 continues to process blocks 445 to 455. In process blocks 445 to 455, dynamic illuminator 205 is operated by controller 215 to generate a non-circular illumination pattern (also referred to as a stacked illumination pattern) for illuminating retina 275 through the pupil of eye 270. FIGS. 6A-C illustrate characteristics of a non-circular illumination pattern where the offset is in a single direction. As illustrated in FIG. 6A, the non-circular illumination pattern enables a single illumination source 601. If the amount of offset in the single direction is small, then the inner most illumination source 601 is illuminated. However, as the amount of offset increases, progressively more peripheral illumination sources are illuminated. FIG. 7A illustrates an example of a non-circular illumination pattern having illumination source 701 enabled due to a more substantial offset alignment in a single direction. Both FIGS. 6A and 7A illustrate examples where retinal imaging system 200 is offset vertically below eye 270. Accordingly, the particular illumination source selected is on the opposite side of center baffle 305 as the physical offset alignment with eye 270 and has an increasing peripheral offset from center baffle 305 with increasing offset alignment. Accordingly, In process block 445, the direction of offset is determined to identify which side of dynamic illuminator 200 will be enabled. In process block 450, the amount of offset is determined to identify which illumination source 325 (e.g., inner, intermediate, outer) will be enabled. Finally, the non-circular illumination pattern is generated in process block 455.

FIG. 6B illustrates the stacked alignment between the illumination path 605 and image path 610, which are substantially separated from each other at the iris, lens, and cornea. Again, center baffle 305 strategically casts an illumination shadow onto these eye structures when an inner most illumination source (such as illumination source 601) is illuminated. This reduces crosstalk between the image path 610 and illumination path 605 to reduce image artifacts captured by image sensor 210.

Figure 7B:
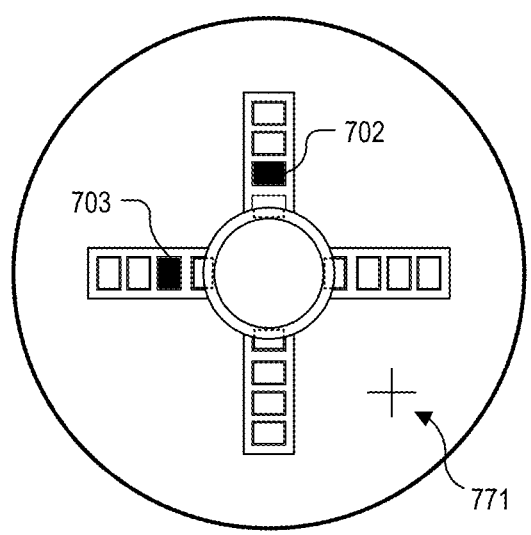
FIG. 7B illustrates a non-circular illumination pattern from the dynamic illuminator when the retinal imaging system is offset from a gaze direction in two directions, in accordance with an embodiment of the disclosure.

FIG. 7B illustrates an example non-circular illumination pattern when retinal imaging system 200 is offset from gaze direction 271 in two directions. For example, in FIG. 7B gaze direction 271 is offset down and to the right, as illustrated by target 771 in FIG. 7B, and thus illumination sources 702 and 703, which are up and to the left are illuminated. Since the amount of offset or misalignment is moderate, illumination sources 702 and 703 are intermediately disposed along their respective illumination arrays.

Figure 8A:
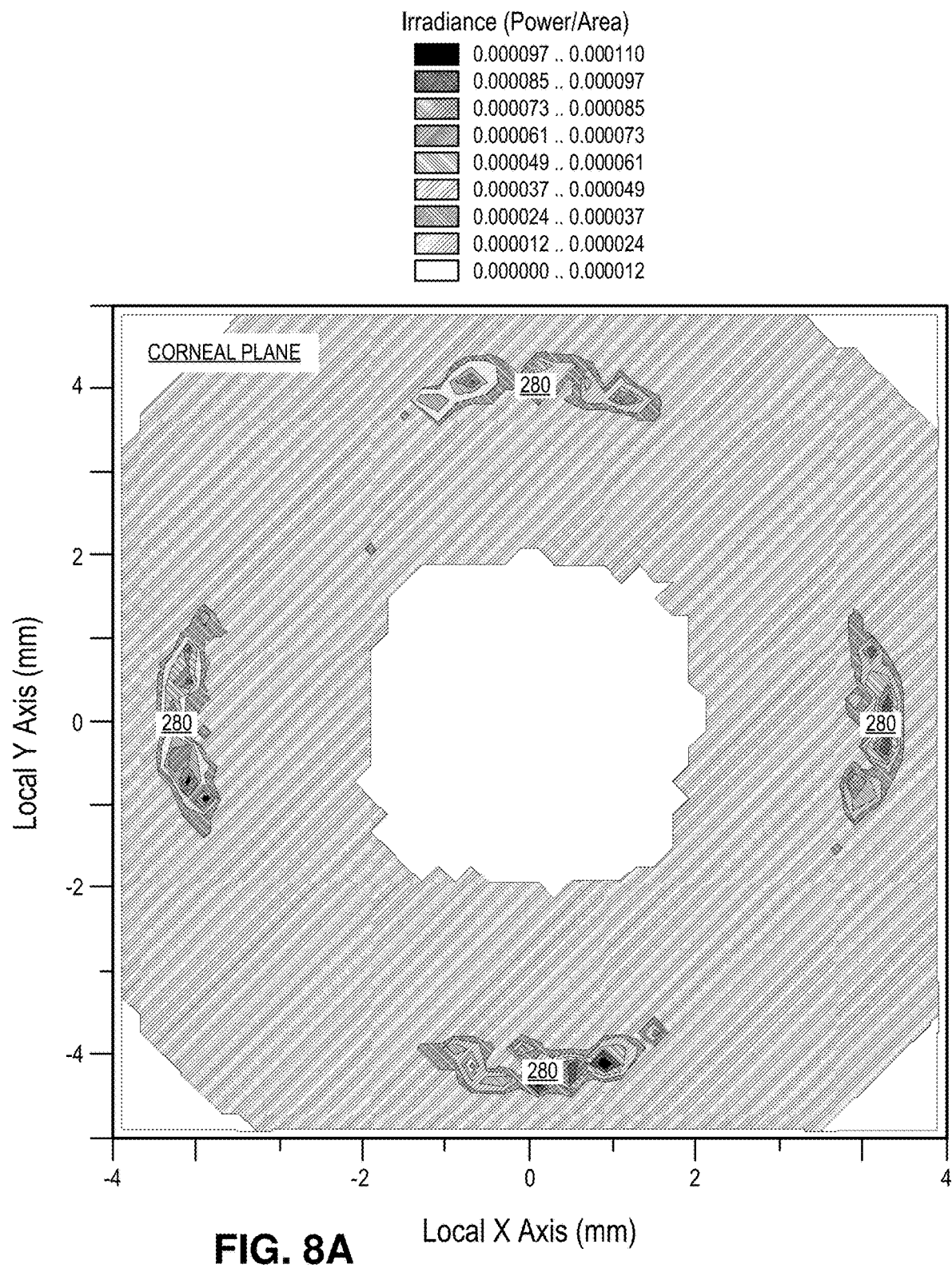
FIG. 8A is a demonstrative heat map illustrating an example cross-section of the illumination path at the corneal plane of the eye, in accordance with an embodiment of the disclosure.
Figure 8B:
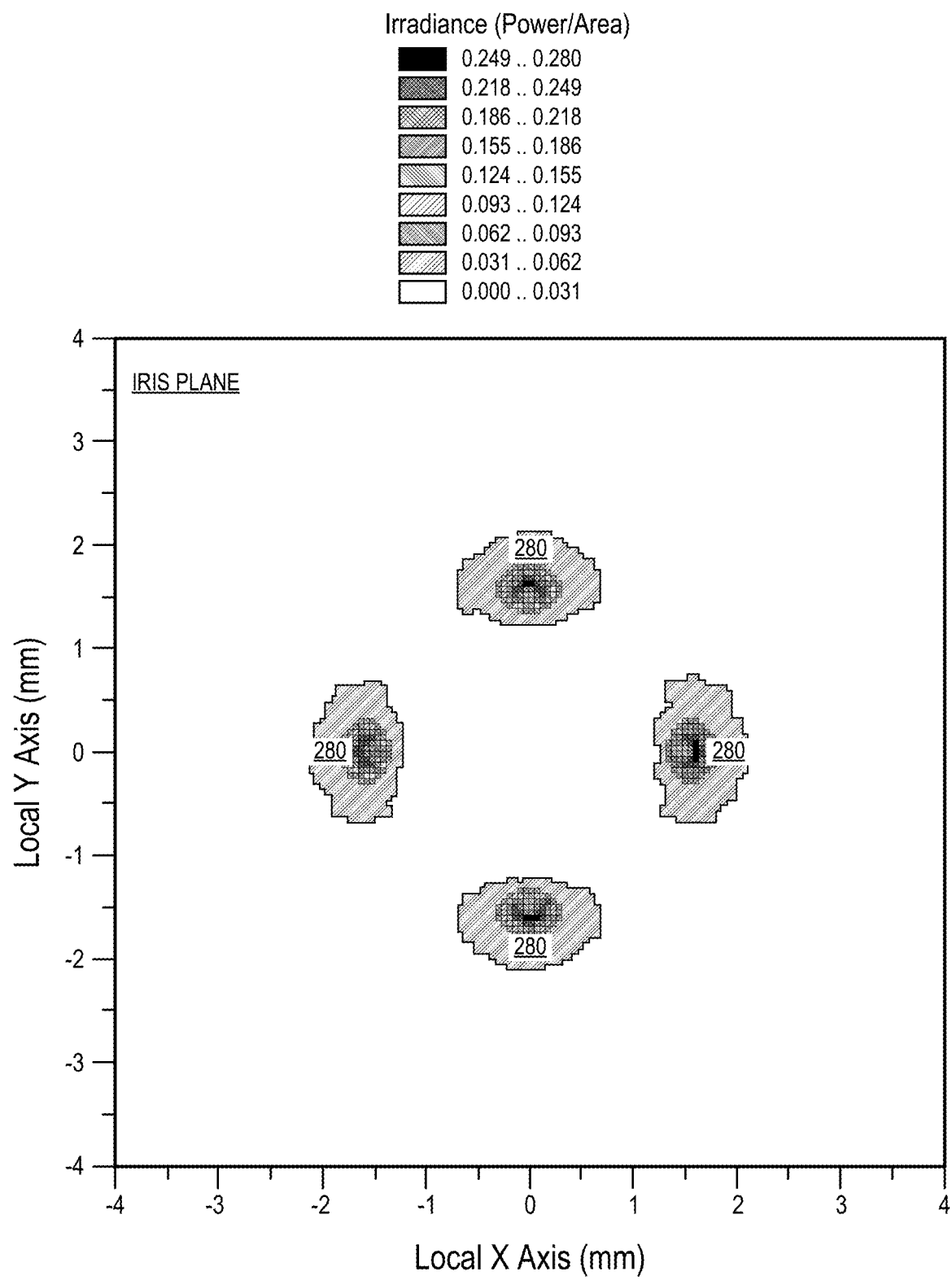
FIG. 8B is a demonstrative heat map illustrating a example cross-section of illumination paths at the iris plane of the eye, in accordance with an embodiment of the disclosure.
Figure 8C:
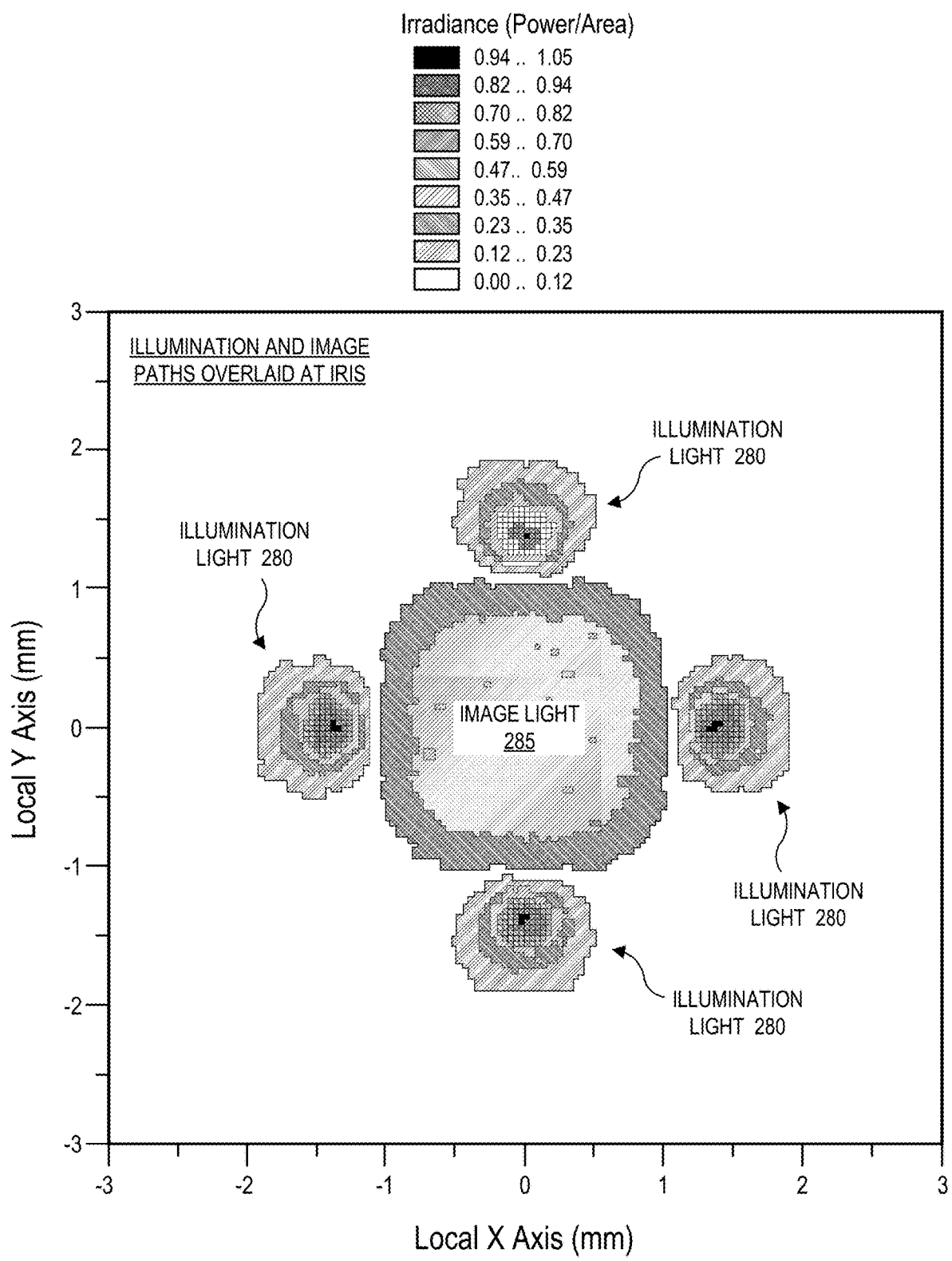
FIG. 8C is a demonstrative heat map illustrating example cross-sections of illumination paths and an image path overlaid at the iris, in accordance with an embodiment of the disclosure.

FIGS. 8A-C are demonstrative heat maps illustrating the physical separations between the image path and the illumination path of a circular illumination pattern at the structures of the eye that cause detrimental reflections and scattering. FIG. 8A illustrates how illumination light 280 is substantially relegated to the peripheral regions at the corneal plane with little or no illumination in the center. FIG. 8B illustrates how illumination light 280 is again substantially relegated to the peripheral regions at the iris plane with little or no illumination in the center. Center baffle 305 casts a shadow down the center of eye 270, creating a center hole with little or no illumination while allowing dynamic illuminator 205 (or 300) to substantially evenly flood iris 275 with illumination. FIG. 8C is a heat map illustrating example cross-sections of illumination light 280 and image light 285 overlaid at the iris. As can be seen, the paths for illumination and imaging are substantially separated at the iris, which reduces crosstalk due to scattering or reflections. Due to the physical separations between these paths, the scattering and/or deleterious reflections that do occur at the various eye structures are more easily blocked by center baffle 305 and aperture 310.

Figure 9A:
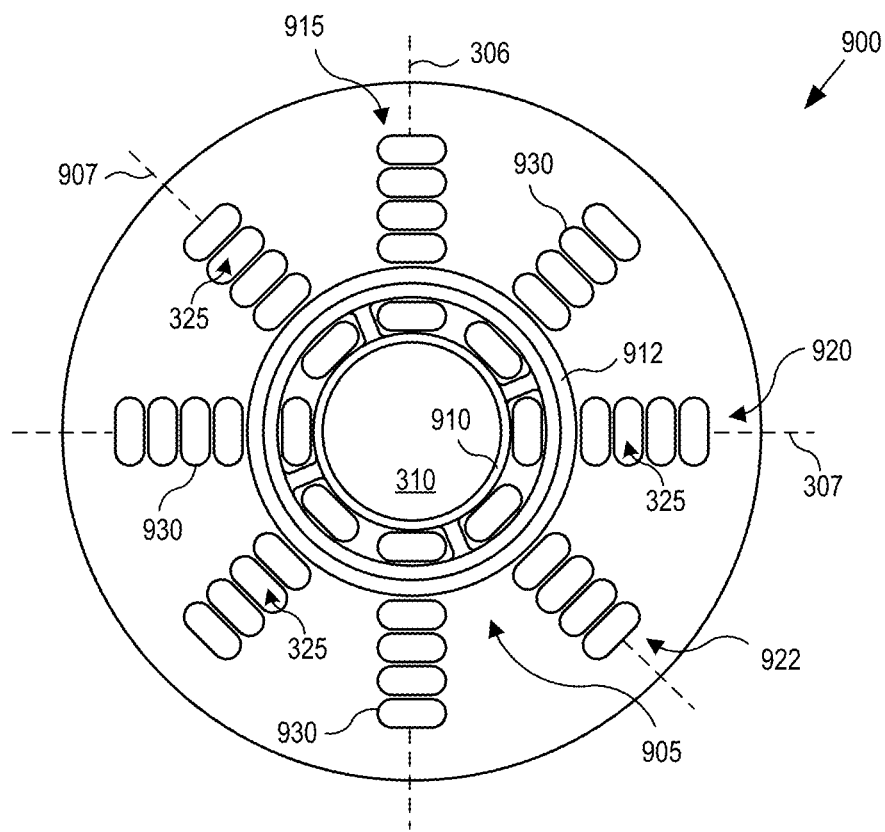
FIGS. 9A & 9B illustrate various views of a dynamic illuminator having a center baffle with dual cylindrical shroud walls, in accordance with an embodiment of the disclosure.
Figure 9B:
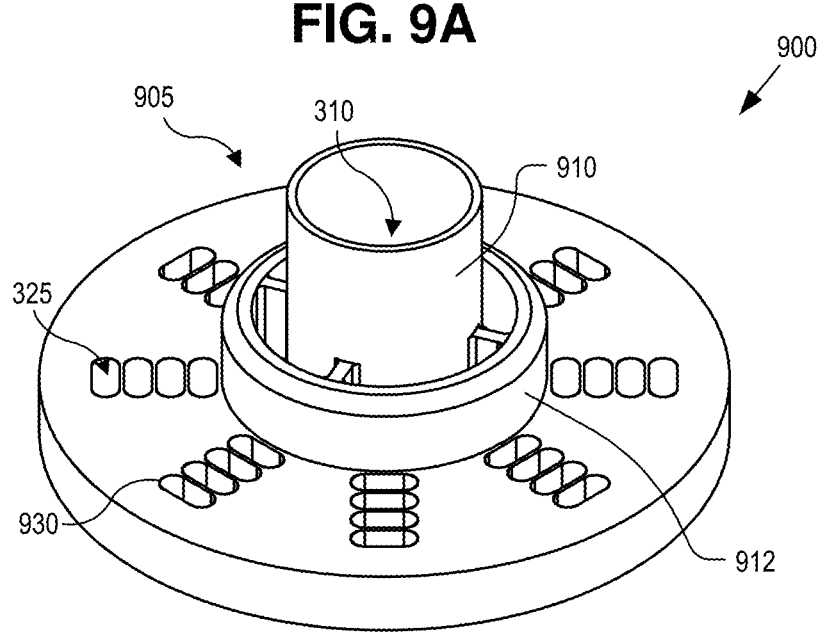

FIGS. 9A and 9B illustrate various views of a dynamic illuminator 900, in accordance with an embodiment of the disclosure. The illustrated embodiment of dynamic illuminator 900 is another possible implementation of dynamic illuminator 205 in FIG. 2. FIG. 9A is a plan view illustration of dynamic illuminator 900 while FIG. 9B is a perspective view illustration of the same. The illustrated embodiment of dynamic illuminator 900 includes a center baffle 905 defining aperture 310, a first illumination array 915 extending out (e.g., radially) from opposing sides of aperture 310 and center baffle 905 along first linear axis 306 (vertical axis in FIG. 9A), a second illumination array 920 extending out (e.g., radially) from opposing sides of aperture 310 and center baffle 905 along second linear axis 307 (horizontal axis in FIG. 9A), and a third illumination array 922 extending out (e.g., radially) from opposing sides of aperture 310 and center baffle 905 along a third linear axis 907 (diagonal axis in FIG. 9A). The illustrated embodiment of center baffle 905 includes cylindrical shroud walls 910 and 912. Each illumination array 915, 920, and 922 includes discrete illumination sources 325 that are each encircled by illumination baffles 930.

Illumination arrays 915, 920, and 922 operate in a similar manner as discussed above in connection with illumination arrays 315 and 320, except that the option additional diagonal illumination array 922 provides additional illumination flexibility. The illustrated embodiment of each illumination array 915, 920, and 922 includes ten discrete illumination sources 325 compared to eight discrete illumination sources 325 for each illumination array 315 and 320. While the number of discrete illumination sources 325 per illumination array may be adjusted, the two additional discrete illumination sources 325 provide finer granular control over the illumination patterns.

Center baffle 905 also operates in a similar functional manner as center baffle 305; however, uses two cylindrical shroud walls 910 and 912 to precisely confine the emission divergence pattern (and strategically cast shadows onto eye 270) as opposed to the single cone shaped center baffle 305. The straight, cylindrical shape of shroud walls 910 and 912 may be simpler to manufacture versus the angled cone shape of center baffle 305. As illustrated, outer cylindrical shroud wall 912 surrounds the inner cylindrical shroud wall 910. Both cylindrical shroud walls 910 and 912 extend from the plane of aperture 310; however, inner cylindrical shroud wall 910 extends to a greater height than outer cylindrical shroud wall 912. Furthermore, the inner most discrete illumination sources 325 of each illumination array 915, 920, and 922 (i.e., the two inner most discrete illumination sources from each illumination array disposed on either side of, and immediately adjacent to, aperture 310) are disposed radially between inner cylindrical shroud wall 910 and outer cylindrical shroud wall 912. The remaining discrete illumination sources 325 are all disposed radially outside of cylindrical shroud wall 912. This intermediate position of inner discrete illumination sources 325 enables cylindrical shroud walls 910 and 912 to confine the inner and outer edges (i.e., emission divergence pattern) of the illumination path output from the inner discrete illumination sources 325. Correspondingly, the heights of cylindrical shroud walls 910 and 912 are also selected to control the inner edge of the illumination paths output from the second inner ring of discrete illumination sources 325 (i.e., discrete illumination sources 325 radially outside of, but immediately adjacent to, cylindrical shroud wall 912).

Figure 10A:
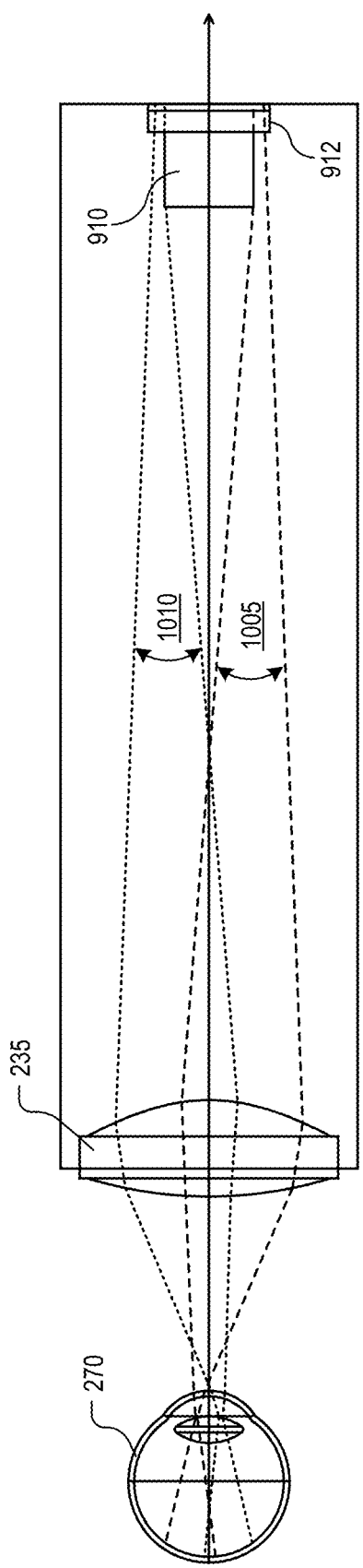
FIGS. 10A & 10B illustrate how the center baffle with dual cylindrical shroud walls confines both sides of the emission divergence of illumination light emitted from the inner most discrete illumination sources, in accordance with an embodiment of the disclosure.
Figure 10B:
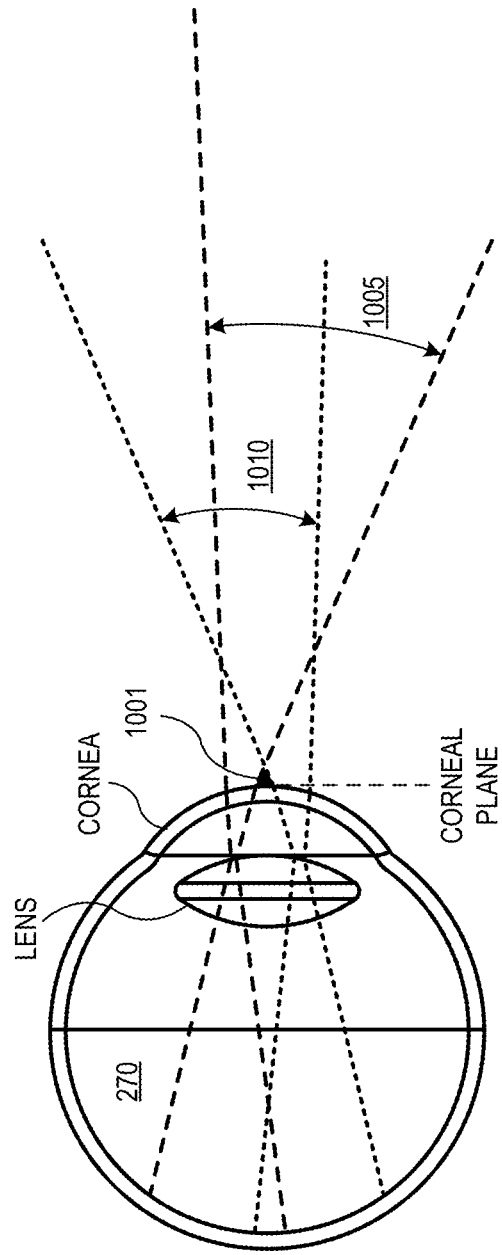

FIGS. 10A & 10B illustrate how center baffle 905 confines both sides of the emission divergence of illumination light emitted from the inner most discrete illumination sources, in accordance with an embodiment of the disclosure. FIG. 10B is a closeup of the portion of FIG. 10A where the illumination paths 1005 and 1010 are incident upon the cornea of eye 270. As illustrated, illumination paths 1005 and 1010 are confined by cylindrical shroud walls 910 and 912 to reduce deleterious reflections at the cornea and lens. In particular, illumination paths 1005 and 1010 are confined to ensure a shadow 1001 is cast at the center of the corneal plane.

Figure 11A:
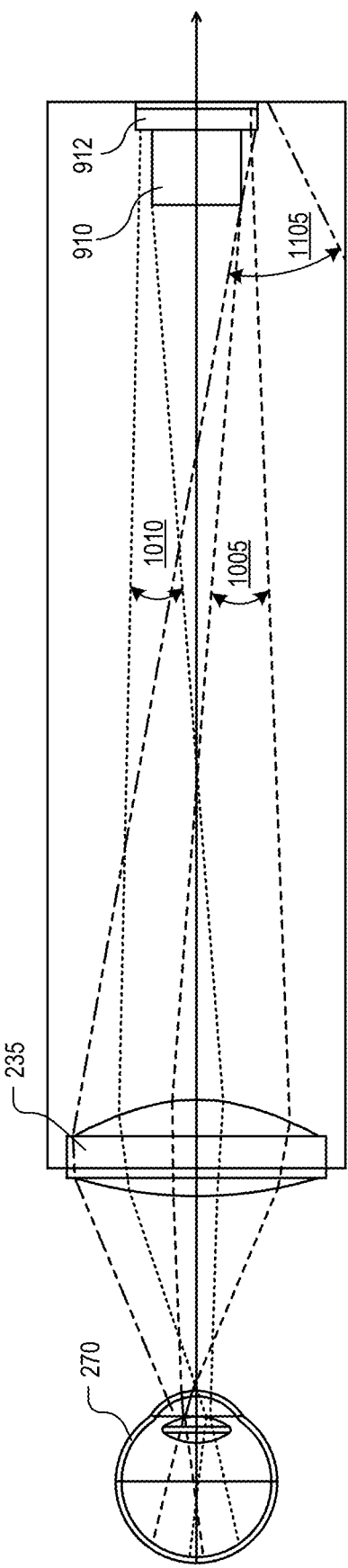
FIGS. 11A & 11B illustrate how the center baffle with dual cylindrical shroud walls confines the inner side of the emission divergence of illumination light emitted from the second inner most discrete illumination sources, in accordance with an embodiment of the disclosure.
Figure 11B:
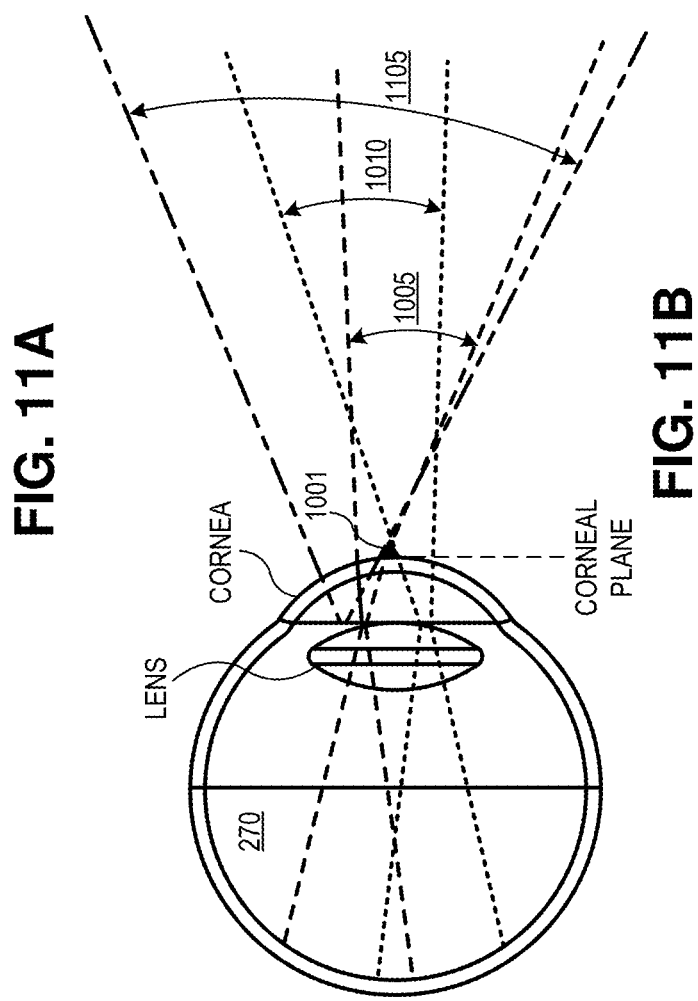

FIGS. 11A & 11B illustrate how center baffle 905 confines the inner side of the emission divergence of illumination light emitted from the second inner most ring of discrete illumination sources, in accordance with an embodiment of the disclosure. FIG. 11B is a closeup of the portion of FIG. 11A where the illumination paths 1005, 1010, and 1105 are incident upon the cornea of eye 270. As illustrated, illumination path 1105 is confined on the inner side (e.g., middle) by the top edges of cylindrical shroud walls 910 and 912. Illumination path 1105 is the emission divergence path of the light output from the second inner most ring of discrete illumination sources 325 (i.e., discrete illumination sources radially outside of, and immediately adjacent to, cylindrical shroud wall 912). In particular, the inner side of illumination path 1105 is confined to also ensure shadow 1001 is cast at the center of the corneal plane. Shadow 1001 reduces deleterious reflections at the cornea and the lens. It should also be appreciated that eyepiece lens 235 is fully illuminated, thus providing improved imaging and illumination.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:
1. A retinal imaging system, comprising:
an image sensor adapted to acquire a retinal image; and
a dynamic illuminator for illuminating a retina to acquire the retinal image, the dynamic illuminator including:

a center baffle that extends from and surrounds an aperture through which an image path for the retinal image passes before reaching the image sensor;

a first illumination array extending out from first opposing sides of the aperture along a first linear axis; and a second illumination array extending out from second opposing sides of the aperture along a second linear axis, substantially orthogonal to the first linear axis.

2. The retinal imaging system of claim 1, wherein the first illumination array extends out radially from the first opposing sides of the aperture along the first linear axis that intersects a center of the aperture and the second illumination array extends out radially from the second opposing sides of the aperture along the second linear axis that also intersects the center of the aperture.

3. The retinal imaging system of claim 1, wherein the first illumination array comprises a plurality of first discrete illumination sources and the second illumination array comprises a plurality of second discrete illumination sources.

4. The retinal imaging system of claim 3, wherein the first and second discrete illumination sources are respectively encircled by corresponding illumination baffles that each constrains an emission divergence pattern of a corresponding one of the first and second discrete illumination sources.

5. The retinal imaging system of claim 3, wherein the center baffle at least partially overlaps inner most ones of the first and second discrete illumination sources that are immediately adjacent to the center baffle and wherein the center baffle is positioned in the retinal imaging system such that the center baffle casts a shadow when the inner most ones of the first and second discrete illumination sources are illuminating.

6. The retinal imaging system of claim 5, wherein an angle and a depth of the center baffle is configured to achieve a particular separation range between the image path and an illumination path at an iris when acquiring the retinal image.

7. The retinal imaging system of claim 3, wherein the first discrete illumination sources are symmetrically positioned about the second linear axis and the second discrete illumination sources are symmetrically positioned about the first linear axis.

8. The retinal imaging system of claim 3, further comprising:

an alignment tracker for tracking alignment between the retinal imaging system and an eye of the retina; and a controller coupled to image sensor, the alignment tracker, and the dynamic illuminator, the controller including logic that when executed by the controller causes the retinal imaging system to perform operations including:

determining an alignment between the retinal imaging system and the eye;

generating a circular illumination pattern with the dynamic illuminator when the retinal imaging system is determined to be approximately centrally aligned with a gaze direction of the eye; and generating a non-circular illumination pattern with the dynamic illuminator when the retinal imaging system is determined to be offset from the gaze direction of the eye.

9. The retinal imaging system of claim 8, wherein generating the circular illumination pattern comprises:

simultaneously illuminating innermost ones of the first and second discrete illumination sources that are immediately adjacent to the center baffle.

10. The retinal imaging system of claim 8, wherein generating the non-circular illumination pattern comprises:

illuminating a single one of the first or second discrete illumination sources when the retinal imaging system is determined to be offset from the gaze direction in a single direction, wherein the single one of the first or second discrete illumination sources is located on an opposite side of the aperture as the offset in the single direction.

11. The retinal imaging system of claim 8, wherein generating the non-circular illumination pattern comprises:

illuminating one of the first discrete illumination sources and one of the second discrete illumination sources when the retinal imaging system is determined to be offset from the gaze direction in two directions, wherein the ones of the first and second discrete illumination sources are located on opposite sides of the aperture as the offset in the two directions, respectively.

12. The retinal imaging system of claim 8, wherein the controller includes further logic that when executed by the controller causes the retinal imaging system to perform further operations including:

smoothly fading the dynamic illuminator between the circular illumination pattern and the non-circular illumination pattern when alignment of the retinal imaging system is determined to transition between a central alignment and an offset alignment.

13. The retinal imaging system of claim 1, wherein the center baffle is cone shaped and has a circular cross-sectional shape.

14. The retinal imaging system of claim 1, wherein the center baffle comprises:

a first cylindrical shroud wall having a first height extending out from a plane of the aperture; and a second cylindrical shroud wall having a second height extending out from the plane of the aperture, wherein the second cylindrical shroud wall surrounds the first cylindrical shroud wall, and wherein the first height is greater than the second height.

15. The retinal imaging system of claim 14, wherein the first and second illumination arrays each include:

two inner discrete illumination sources disposed radially between the first and second cylindrical shroud walls; and a plurality of outer discrete illumination sources disposed radially outside of the second cylindrical shroud wall.

16. A method of imaging a retina, comprising:

monitoring an alignment between a retinal imaging system and an eye;

generating a circular illumination pattern with a dynamic illuminator when the retinal imaging system is determined to be centrally aligned with a gaze direction of the eye;

generating a non-circular illumination pattern with the dynamic illuminator when the retinal imaging system is determined to be offset from the gaze direction of the eye; and acquiring the image light of the retina with an image sensor of the retinal imaging system.

17. The method of claim 16, wherein the dynamic illuminator comprises:

first discrete illumination sources extending radially out from first opposing sides of a center baffle along a first linear axis; and second discrete illumination sources extending radially out from second opposing sides of the center baffle along a second linear axis, substantially orthogonal to the first linear axis.

18. The method of claim 17, further comprising:
- passing the image light of the retina along an image path through an aperture surrounded by the center baffle to the image sensor; and
- blocking at least a portion of image artifacts from reaching the image sensor with the center baffle, wherein the image artifacts are due to at least scattering or specular reflection of illumination light from the dynamic illuminator.

19. The method of claim 18, further comprising:
- casting a shadow into the eye with the center baffle by blocking a portion of illumination light emitted from innermost ones of the first and second discrete illumination sources that are immediately adjacent to the center baffle, wherein the shadow reduces the image artifacts reaching the image sensor.

20. The method of claim 17, wherein generating the circular illumination pattern comprises:
- simultaneously illuminating innermost ones of the first and second discrete illumination sources that are immediately adjacent to the center baffle.

21. The method of claim 17, wherein generating the non-circular illumination pattern comprises:
- illuminating one of the first or second discrete illumination sources when the retinal imaging system is determined to be offset from the gaze direction in a single direction, wherein the one of the first or second discrete illumination sources is located on an opposite side of the center baffle as the offset in the single direction.

22. The method of claim 21, wherein generating the non-circular illumination pattern comprises:
- illuminating one of the first discrete illumination sources and one of the second discrete illumination sources when the retinal imaging system is determined to be offset from the gaze direction in two directions, wherein the ones of the first and second discrete illumination sources are located on opposite sides of the center baffle as the offset in the two directions, respectively.

23. The method of claim 21, wherein the one of the first or second discrete illumination sources is selected with greater peripheral offset from the center baffle as the offset in the single direction increases.

24. The method of claim 17, further comprising:
- constraining emission divergence patterns of the first and second illumination sources with illumination baffles that encircle each of the first and second illumination sources.

25. The method of claim 16, wherein monitoring the alignment between the retinal imaging system and the eye comprises monitoring when the alignment transitions between being centrally aligned and being offset.

26. The method of claim 16, wherein monitoring the alignment includes continuously redetermining whether the alignment is centrally aligned or offset.

27. The method of claim 16, wherein generating the circular illumination pattern includes simultaneously illuminating innermost ones of discrete illumination sources of the dynamic illuminator that are immediately adjacent to an aperture through which image light of the retina passes, and
- wherein generating the non-circular illumination pattern includes generating the non-circular illumination pattern by not illuminating at least one of the innermost ones of the discrete illumination sources of the dynamic illuminator that are immediately adjacent to the aperture.

28. A method of imaging a retina, comprising:
- monitoring an alignment between a retinal imaging system and an eye;
- generating a circular illumination pattern with a dynamic illuminator when the retinal imaging system is determined to be centrally aligned with a gaze direction of the eye;
- generating a non-circular illumination pattern with the dynamic illuminator when the retinal imaging system is determined to be offset from the gaze direction of the eye;
- acquiring image light of the retina with an image sensor of the retinal imaging system; and
- smoothly fading the dynamic illuminator between the circular illumination pattern and the non-circular illumination pattern when alignment of the retinal imaging system is determined to transition between a central alignment and an offset alignment.

* * * * *

UNITED STATES PATENT AND TRADEMARK OFFICE
CERTIFICATE OF CORRECTION

PATENT NO. : 11,202,567 B2
APPLICATION NO. : 16/457191
DATED : December 21, 2021
INVENTOR(S) : E. Glik et al.

It is certified that error appears in the above-identified patent and that said Letters Patent is hereby corrected as shown below:

In the Claims

| Column | Line | |
|---|---|---|
| 11 | 46 | In Claim 8, change "to image" to -- to the image --. |

Signed and Sealed this
Twenty-first Day of February, 2023

Katherine Kelly Vidal
*Director of the United States Patent and Trademark Office*